US011484381B2

United States Patent
Pak et al.

(10) Patent No.: US 11,484,381 B2
(45) Date of Patent: Nov. 1, 2022

(54) INSTRUMENT ALIGNMENT FEEDBACK SYSTEM AND METHOD

(71) Applicant: Ruthless, LLC, Irwindale, CA (US)

(72) Inventors: Shane S. Pak, Arcadia, CA (US); Karlton E. Spindle, Cedar Glen, CA (US)

(73) Assignee: Ruthless, LLC, Irwindale, CA (US)

( * ) Notice: Subject to any disclaimer, the term of this patent is extended or adjusted under 35 U.S.C. 154(b) by 23 days.

(21) Appl. No.: 16/140,487

(22) Filed: Sep. 24, 2018

(65) Prior Publication Data

US 2019/0388173 A1 Dec. 26, 2019

Related U.S. Application Data

(60) Provisional application No. 62/763,564, filed on Jun. 21, 2018.

(51) Int. Cl.
*A61B 90/00* (2016.01)

(52) U.S. Cl.
CPC ............. *A61B 90/06* (2016.02); *A61B 90/08* (2016.02); *A61B 2090/067* (2016.02); *A61B 2090/0811* (2016.02)

(58) Field of Classification Search
CPC ....... A61B 5/103; A61B 5/1071; A61B 90/06; A61B 2090/067; A61B 90/08; A61B 2090/0811
See application file for complete search history.

(56) References Cited

U.S. PATENT DOCUMENTS

| | | | |
|---|---|---|---|
| 8,442,621 B2 | 5/2013 | Gorek et al. | |
| 8,981,914 B1* | 3/2015 | Stetten | A61B 42/10 340/407.1 |
| 9,814,393 B1 | 11/2017 | Mao et al. | |
| 10,792,108 B2 | 10/2020 | Yang et al. | |
| 2005/0267358 A1* | 12/2005 | Tuma | A61B 90/39 600/414 |
| 2009/0163901 A1 | 6/2009 | Fisher et al. | |
| 2010/0100130 A1 | 4/2010 | Carl et al. | |
| 2010/0249658 A1* | 9/2010 | Sherman | A61B 5/103 600/587 |
| 2012/0179070 A1* | 7/2012 | Pommer | A61B 5/6848 600/594 |
| 2014/0246917 A1* | 9/2014 | Proud | A61B 5/332 307/104 |
| 2017/0231709 A1 | 8/2017 | Gupta et al. | |
| 2018/0280065 A1 | 10/2018 | Babic et al. | |
| 2019/0388155 A1 | 12/2019 | Cattin et al. | |
| 2019/0388173 A1 | 12/2019 | Pak et al. | |
| 2021/0228279 A1 | 7/2021 | Dorman | |
| 2022/0039877 A1 | 2/2022 | Frasier et al. | |

FOREIGN PATENT DOCUMENTS

| | | |
|---|---|---|
| DE | 10 2012 218 010 | 4/2014 |
| WO | WO 2016/131016 A3 | 8/2016 |
| WO | WO 2017/116751 A3 | 7/2017 |

* cited by examiner

*Primary Examiner* — Julianna N Harvey
(74) *Attorney, Agent, or Firm* — Maceiko IP

(57) ABSTRACT

A system to measure and display the orientation of a handheld instrument is disclosed.

28 Claims, 12 Drawing Sheets

Accurate Placement

Lateral Breach

Medial Breach

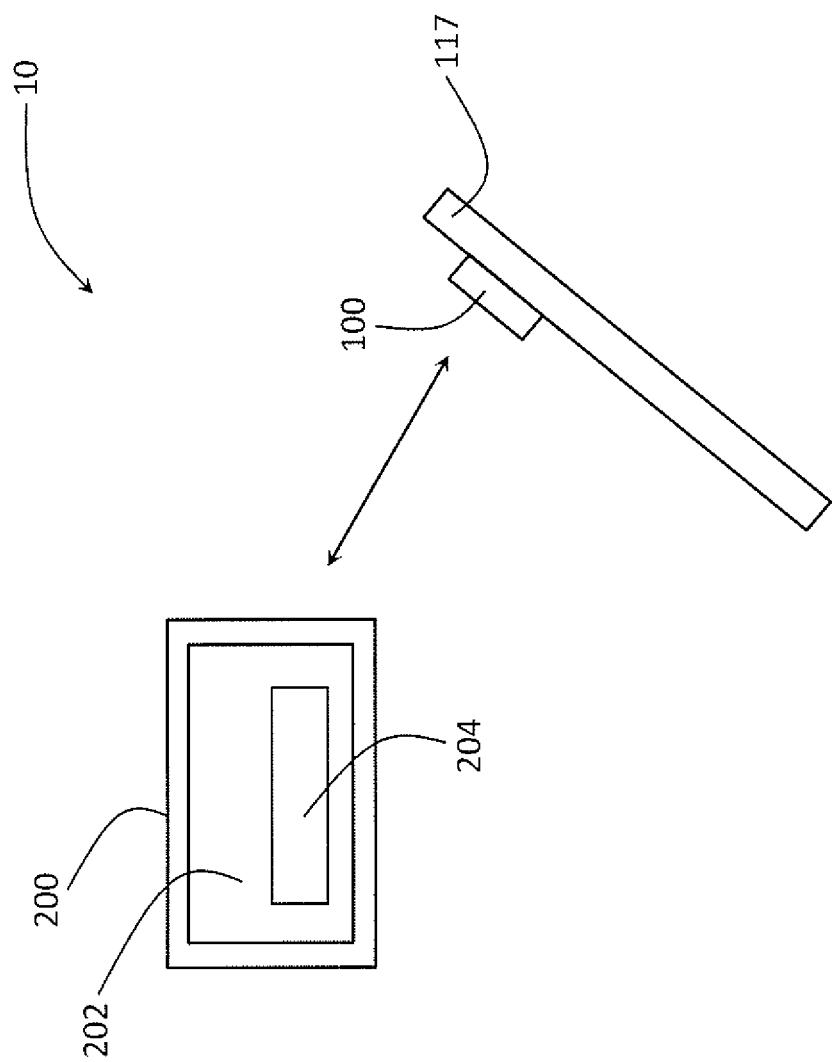

INSTRUMENT ALIGNMENT FEEDBACK SYSTEM AND METHOD

CROSS-REFERENCE TO RELATED APPLICATION

This application claims the benefit of U.S. Provisional Application No. 62/763,564, filed Jun. 21, 2018, the contents of which are incorporated herein by reference.

COPYRIGHT STATEMENT

This patent document contains material subject to copyright protection. The copyright owner has no objection to the reproduction of this patent document or any related materials in the files of the United States Patent and Trademark Office, but otherwise reserves all copyrights whatsoever.

FIELD OF THE INVENTION

This invention relates to the alignment of instruments, including the angular alignment of surgical instruments such as those used in spinal stabilization surgeries.

BACKGROUND OF THE INVENTION

Thousands of spinal stabilization surgeries are performed every year. During the procedures, stabilizing structures, such as spinal rods and/or plates, are implanted to provide support to the patient's spine. The procedures may also involve the use of pedicle screws that may be embedded into the patient's spine to secure the rods/plates.

The implantation of the pedicle screws may involve first drilling a pilot hole through the pedicle and into the vertebral body of the patient's spine. The pedicle screw may then be implanted into the pilot hole.

In order to properly place the pedicle screw and avoid damaging the patient's spinal column, the position, angular orientation and trajectory of the pilot hole must be precisely executed.

Imaging instrumentation (such as fluoroscopic imaging systems) may provide images of the patient's spine to assist in the placement of the pilot holes, but the images may be limited in the real time information that they may provide during the procedure. In addition, the use of such systems may expose the patient and the doctors/nurses to high levels of ionized radiation, such that extended use of such systems may be undesirable. Also, a skilled surgeon may rely on his/her experience in order to properly place the pilot holes, but the experience level of each surgeon may vary and may not be adequate in many cases.

In fact, studies have shown that up to 4% of pedicle screws implanted during spinal stabilization surgeries may be misaligned. Such misalignment may cause significant health complications to the patients and in many cases the pedicle screws may require revision, thus requiring additional surgeries.

Other types of surgical/medical procedures may also require the precise alignment of the surgical instruments used. For example, hypodermic needles may often times require proper positioning and alignment during use.

Accordingly, there is a need for a system and method that provides real time feedback regarding the angular orientation, position and trajectory of surgical instruments.

SUMMARY OF THE INVENTION

The present invention is specified in the claims as well as in the below description.

In one embodiment, a system for providing feedback regarding the orientation of a handheld instrument may include at least one measurement sensor configured with the handheld instrument, and a controller in communication with the at least one measurement sensor; wherein the at least one measurement sensor may measure the orientation of the instrument, and the controller may provide feedback based on the measured orientation.

In one aspect, the instrument may be selected from the group: an awl, a probe, a tap, a drill, a screw driver, a scalpel and a hypodermic needle.

In another aspect, the at least one measurement sensor may include at least one accelerometer.

In another aspect, the at least one measurement sensor may include at least one gyroscope.

In another aspect, the measured orientation may be an orientation in three-dimensional space.

In one embodiment, an assembly adapted to measure the orientation of a surgical instrument may include at least one measurement sensor configured with the surgical instrument; wherein the at least one measurement sensor may measure the angular orientation of the surgical instrument, and output a signal based on the measured angular orientation.

In one aspect, the assembly may include a controller in communication with the at least one measurement sensor, wherein the controller may receive the signal and provide feedback based on the measured angular orientation of the surgical instrument.

In another aspect, the surgical instrument may be a handheld instrument.

In another aspect, the surgical instrument may be selected from the group: an awl, a probe, a tap, a drill, a screw driver, a scalpel and a hypodermic needle.

In another aspect, the at least one measurement sensor may include at least one accelerometer.

In another aspect, the at least one measurement sensor may include at least one gyroscope.

In another aspect, the measured orientation may be an orientation in three-dimensional space.

In one embodiment, a handheld surgical instrument adapted to provide feedback regarding its orientation may include at least one measurement sensor configured with the surgical instrument; wherein the at least one measurement sensor may measure the angular orientation of the surgical instrument, and output a signal based on the measured angular orientation.

In one aspect, the surgical instrument may also include a controller in communication with the at least one measurement sensor, wherein the controller may receive the signal and provide feedback based on the measured angular orientation of the surgical instrument.

In another aspect, the surgical instrument may be selected from the group: an awl, a probe, a tap, a drill, a screw driver, a scalpel and a hypodermic needle.

In another aspect, the at least one measurement sensor may include at least one accelerometer.

In another aspect, the at least one measurement sensor may include at least one gyroscope.

In another aspect, the measured angular orientation may be an orientation in three-dimensional space.

In one embodiment, a method for aligning a handheld surgical instrument that may include at least one measurement sensor and a controller in communication with the at least one measurement sensor, may include:

(A) configuring the at least one measurement sensor with the surgical instrument;

(B) using the at least one measurement sensor to measure the angular orientation of the surgical instrument;

(C) providing the measured angular orientation information in (B) to the controller; and (D) using the controller to provide feedback based on the angular orientation information.

In one aspect, the method may also include:

(E) aligning the surgical instrument based on the feedback provided in (D).

A person of ordinary skill in the art will understand, that any method described above or below and/or claimed and described as a sequence of steps is not restrictive in the sense of the order of steps.

BRIEF DESCRIPTION OF THE DRAWINGS

Various objects, features and attendant advantages of the present invention will become fully appreciated when considered in conjunction with the accompanying drawings, in which like reference characters designate the same or similar parts throughout the several views, and wherein:

FIG. 3 shows aspects of an alignment feedback system according to exemplary embodiments hereof;

DETAILED DESCRIPTION OF THE PREFERRED EMBODIMENTS

In general, the system according to exemplary embodiments hereof provides devices, tools, instrumentation, software and methods to assist in the proper alignment of devices. The devices to be aligned may include hand tools and/or instruments of any kind, for example, including but not limited to: surgical instruments, hand drills, screw drivers, awls, probes, taps, saws, files, plyers, tweezers, scalpels, hypodermic needles and other types of hand held devices, non-hand held devices and tools. It will be understood by a person of ordinary skill in the art, upon reading this specification, that the system and method may be used with any type of device that may benefit from being aligned in one, two or three dimensions, and that the scope of the system and method is not limited in any way by the types of devices that it may be used with.

For the purpose of this specification and for demonstration, the system and method will be described in relation to its use with surgical instruments (e.g., instruments used for orthopedic surgery). However, it is appreciated that the system and method may be applied to and used with any type of device that may benefit from it.

Referring now to FIGS. 1-12, the system 10 according to exemplary embodiments hereof will be described in further detail. In a presently preferred implementation, the system 10 may be used to provide feedback relating to the three-dimensional navigation and alignment of handheld surgical instruments. In one presently preferred implementation, the surgical instruments may include instruments used to perform orthopedic surgery, e.g., spinal stabilization surgery.

Figure 1:
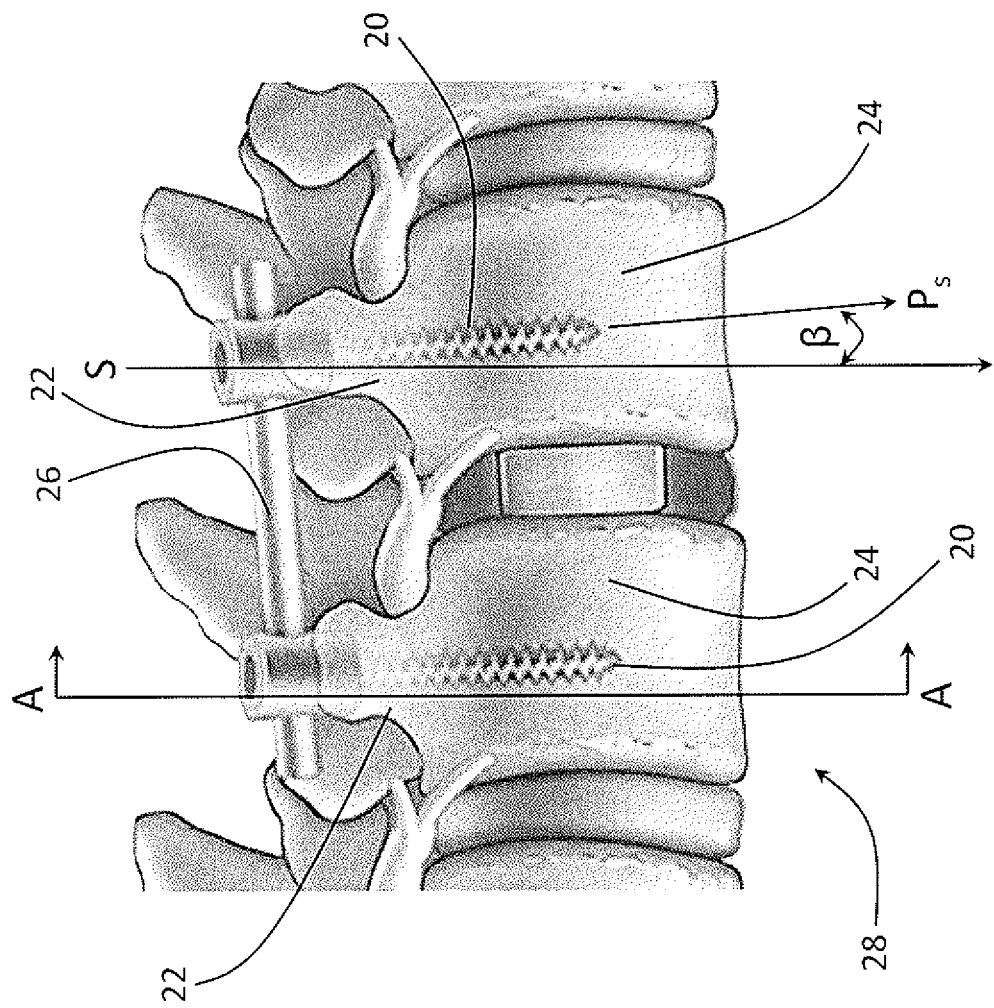
FIG. 1 shows aspects of a pedicle screw and rod according to exemplary embodiments hereof.

In one implementation, the surgical instruments may include devices used to implant pedicle screws into a patient's spine. As shown in FIG. 1, the pedicle screws 20 may preferably be implanted through the pedicle 22 and into the vertebral body 24 of the patient. A linkage unit 26 (e.g., a spinal rod or plate) may then be attached to the pedicle screws 20. Two or more pedicle screws 20 may typically be used to secure each rod/plate 26 (e.g., one pedicle screw 20 on each end of each rod 26) so that the rod/plate 26 may be generally oriented parallel to the spinal column 28 of the patient. In this way, the linkage 26 may be held secure by the pedicle screws 20 and provide stability to the particular segment of the spine on which it may be attached.

It may be preferable that the spinal rod 26 be intraoperatively contoured during the surgical procedure to properly fit between the implanted pedicle screws 20. For instance, it may be preferable to use an intraoperative spinal rod contouring system as described in U.S. Provisional Application No. 62/762,478 filed May 7, 2018, and U.S. application Ser. No. 16/140,491, entitled Surgical Implant Preparation System and Method, filed on even date herewith, the entire contents of which are incorporated herein for any purposes.

The sagittal angle $\beta$ of the right pedicle screw 20 is shown in FIG. 1. The angle $\beta$ of the angular trajectory $P_s$ of the pedicle screw 20 may be measured with respect to the vertical axis S (e.g., the vertical plumb line) along the sagittal plane. The placement of the pedicle screws 20 in FIG. 1 may be deemed as accurate as the screws 20 pass from the pedicle 22 into the vertebral body 24 without perforating any cortical walls.

Figure 2A:
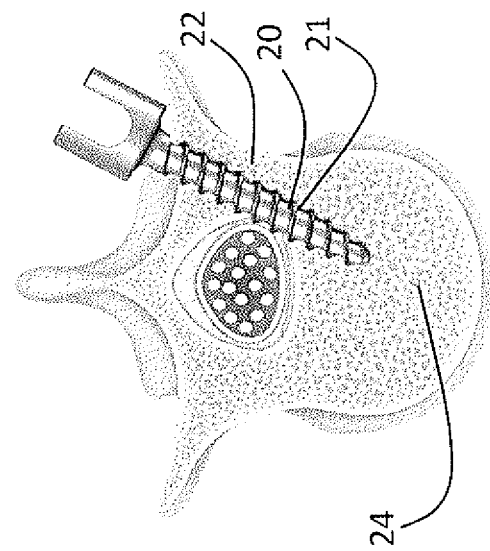
FIGS. 2A, 2B and 2C show the manners in which a pedicle screw may be implanted, e.g., properly as in FIG. 2A according to exemplary embodiments hereof; and improperly as in FIGS. 2B-2C.
Figure 2B:
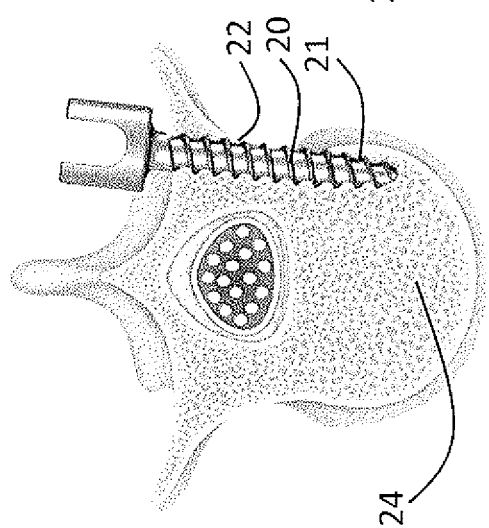
Figure 2C:
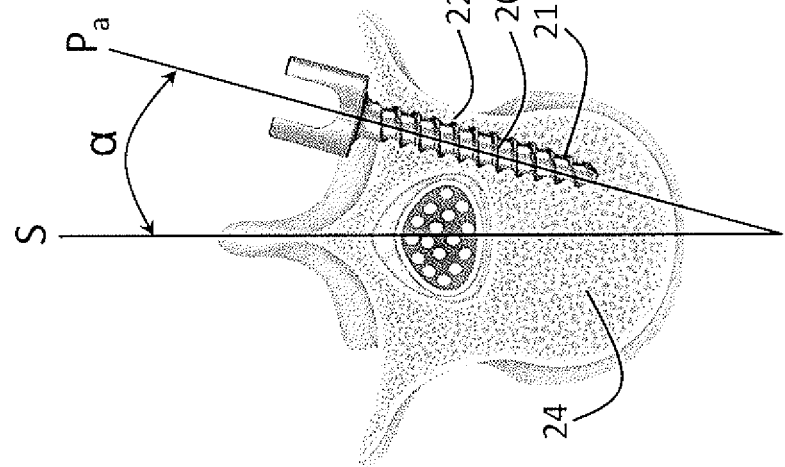

FIGS. 2A, 2B and 2C are taken from the perspective along cut line A-A in FIG. 1 (along the axial or transverse plane).

FIG. 2A shows a pedicle screw 20 within a pilot hole 21 and with an axial angle $\alpha$ (lateral to medial trajectory). The angle $\alpha$ of the angular trajectory $P_a$ of the pedicle screw 20 may be measured with respect to the vertical axis S (e.g., the vertical plumb line) along the axial plane. The placement of the screw 20 may be deemed as accurate as it passes through the pedicle 22 and into the vertebral body 24 without breaching and/or perforating the lateral or medial cortical walls.

FIG. 2B depicts a pedicle screw 20 within a pilot hole 21 breaching and/or perforating the lateral cortical wall, and FIG. 2C depicts a pedicle screw 20 within a pilot hole 21 breaching and/or perforating the medial cortical wall. The pedicle screw placements shown in FIGS. 2B and 2C are deemed inaccurate, and may cause significant neurological problems for the patient, including but not limited to, chronic pain, numbness, limited mobility and paralysis. Thus, depending on the patient's neurological symptoms, inaccurately placed pedicle screws 20 may need to be revised with an additional surgery, adding additional risks and complications to the patient.

In addition, given that the linkage unit 26 may be secured between two or more pedicle screws 20 (as shown in FIG. 1), it can be seen that the pedicle screws 20 may also be required to be properly aligned with respect to one another such that the linkage unit 26 may safely pass between the pedicle screws 20 without obstruction and without applying undesired strain or torque onto the screws 20 or onto the patient's spinal column 28.

Given these considerations, it can be understood that an accurate lateral to medial and cephalic to caudal trajectory and alignment for each pedicle screw 20 is paramount for a successful surgical outcome.

The System

In one exemplary embodiment hereof, the system 10 may include a measurement assembly 100, a controller 200 and other elements, components and mechanisms as necessary to perform its various functionalities. As shown in FIG. 3, the measurement assembly 100 may be configured with an instrument 117 (e.g., a hand tool) that may require proper alignment. In general, the measurement assembly 100 may measure the real time three-dimensional position, orientation and trajectory of the instrument. In this way, the user of the instrument may utilize this positional information to ensure that the instrument is in the proper orientation during its use. As such, for example, the instrument 117 associated with implanting the pedicle screws 20 may be properly aligned so that the pedicle screws 20 may be implanted correctly as shown in FIG. 2A.

The controller 200 may be in communication with the measurement assembly 100 and may generally receive information and data from the measurement assembly 100, and send information and data to the measurement assembly 100. The controller 200 may also process information received from the measurement assembly 100 and provide feedback to the user of the system 10 based on the information received. The controller 200 may also receive inputs from the user as well as interface with other systems including other controllers and systems.

The controller 200 may include any type of controller 200 including but not limited to: a tablet computer, a smartphone, a mobile device, a laptop computer, a PC, a networked controller, a server (e.g., a network, backend or cloud platform), a micro-controller and any other types or combinations of types of controller 200. The controller 200 may include one or more displays 202 that may be used to display data, feedback or other types of information. The controller 200 may also include one or more interfaces 204 (such as touchscreens, keyboards, mouse, etc.) that may be used by the user to interact with the controller 200 (e.g., for data input).

Using spinal stabilization surgery as an example implementation, a surgeon may utilize a surgical hand tool 117 (e.g., an awl) that may be configured with the measurement assembly 100. In one example, the awl may be used to prepare a pilot hole within the patient's spine for insertion of a pedicle screw 20. The measurement assembly 100 may, in real time, measure the three-dimensional position, alignment, orientation and trajectory of the awl, and may provide this positional data to the controller 200.

The controller 200 may then process the data and provide feedback (e.g., visual, textual, audible, etc.) to the surgeon regarding the trajectory of the awl and thus, that of the resulting pilot hole. In this way, the surgeon may utilize real time feedback from the system 10 in order to accurately guide the awl in the correct orientation to result in a properly oriented pilot hole. The pedicle screw 20 may then be inserted into the pilot hole and be thereby properly positioned.

It is understood that the above example is meant for demonstration, and that the system 10 may be used with other types of instruments performing other types of procedures.

The various elements of the system 10 will next be described in further detail.

The Measurement Assembly

Figure 4:
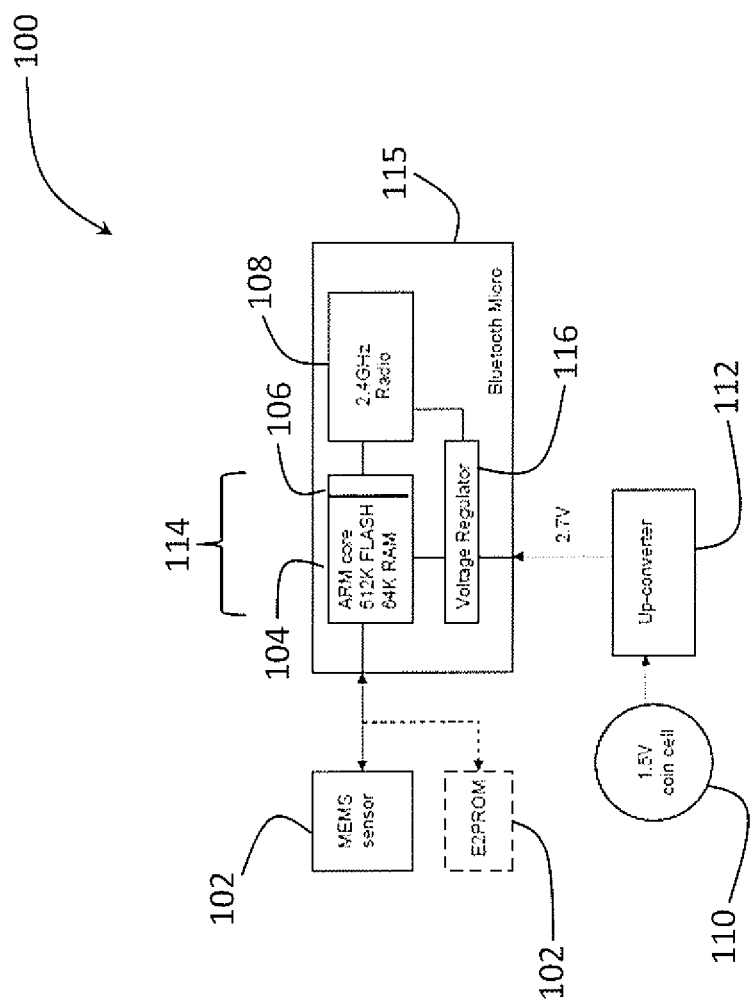
FIGS. 4-6 show aspects of a measurement assembly according to exemplary embodiments hereof.
Figure 5:
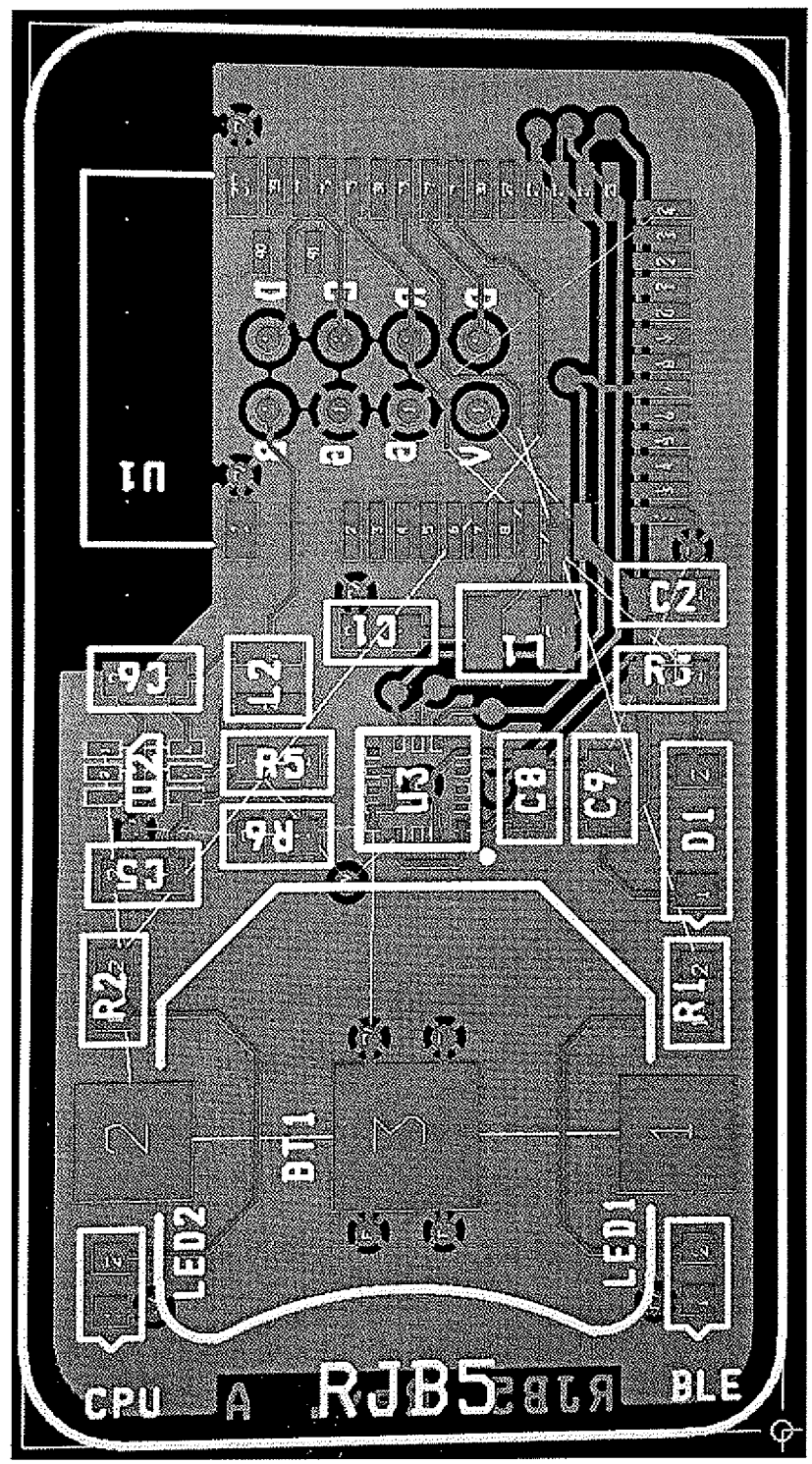

Referring to FIG. 4, according to exemplary embodiments hereof, the measurement assembly 100 may generally include at least one sensor 102, at least one processor 104, memory 106, at least one radio 108, a power supply 110, a voltage converter 112 and other components and elements that may be necessary for the assembly 100 to perform its desired functionalities. Depending on the application of the instrument 117 and of the measurement assembly 100, the assembly 100 may include some or all of the elements described above, and/or additional elements as required.

The sensor 102 may include any type of sensor 102 that may measure, sense or otherwise allow for the determination of the one, two or three-dimensional orientation of the assembly 100. In one exemplary embodiment hereof, the sensor 102 may be an accelerometer, such as a tri-axial (three-axis) micro-electro-mechanical system (MEMS) accelerometer. As is known in the art, an accelerometer 102 may measure both dynamic and static acceleration. By measuring the amount of static acceleration due to terrestrial gravity, the orientation (angle and/or tilt) of the sensor 102 may be determined.

A tri-axial MEMS accelerometer 102 may provide simultaneous measurements in three orthogonal directions, thus providing three-dimensional orientation and trajectory information. The output of the accelerometer 102 may be an electrical charge (e.g., a voltage waveform) that may be proportional to the force exerted on it at any given moment in time. This electrical charge may then be processed to provide real time positional and trajectory data of the unit 100.

The sensor(s) 102 may include piezoelectric, piezoresistive, capacitive or other components to convert mechanical or physical motion into an electrical signal. In one example, the sensor 102 may include three micro-machined pivot arms that may deflect upon acceleration (e.g., gravity). The deflection may be detected by a capacitive sensor and converted into a numerical value (e.g., in units of micro-g or μg). In another example, the sensor 102 may include one or more cantilever beams each with a proof mass (also referred to as a seismic mass) that may deflect under the influence of external accelerations. In another example, the sensor may include one or more gyroscopes (preferably MEMS gyroscopes). Other types and architectures of sensors 102 may also be used, and it is understood that the scope of the system 10 and of the measurement assembly 100 is not limited in any way by the types of sensors 102 that the assembly 100 may utilize.

In one presently preferred implementation, the sensor 102 may be a three-axis accelerometer manufactured by STMicroelectronics (e.g., part number LIS3DSH). It is understood that other sensors 102 manufactured by other manufacturers may also be used.

In one exemplary embodiment hereof, the processor 104 and the memory 106 may be formed together as a microcontroller 114. The microcontroller 114 may also include programmable input/output peripherals as well as other elements such as a voltage regulator 116. The microcontroller 114, radio 108, voltage regulator 116 (as well as other elements and components) may be provided as an integrated system-on-a-chip (SoC) 115. In this way, the unit 100 may be reduced in size. FIG. 4 shows one presently preferred electrical layout of the assembly 100. Note however that other electronic layouts may also be used. In one example, the device 100 may measure 0.8 inches×1.5 inches×0.5 inches, but the device 100 may also be formed in other sizes.

The radio 108 may be a Bluetooth radio that may transmit and receive information at 2.45 GHz to and from the controller 200 (and/or to and from other devices). In one presently preferred implementation the radio 108 may have an output power of 0.0023 watts (e.g., Bluetooth low energy protocol), but other output powers may also be used. In addition, the transmission rate may be 1-2 times per second, but other transmission rates may also be used.

The radio 108 may also be any other kind of radio 108 or combinations of radios 108 that may transmit and receive information at any other frequencies using any types of communication protocols, analog or digital, or any combination thereof. For example, the radio 108 may utilize RF, millimeter wave, Wi-Fi, LAN, WAN, Internet, cellular connectivity, telephony, IR or other types of communication protocol or methods. The radio 108 may also include an antenna, I/O ports and any other type of communications mechanisms as necessary.

In one presently preferred implementation, the transmitter 108 may be manufactured by Raytac Corp. (e.g., part number MDBT42Q, FCC identifier SH6MDBT42Q, certificate number 162181172/AA/00). It is understood that other transmitters 108 manufactured by other manufacturers may also be used.

The power supply 110 may preferably be a battery but may also comprise other types of power storage devices. In one example, the battery 110 may be a 1.5 v coin cell and the voltage converter 112 may be a DC-DC converter 112 that may boost the 1.5 v to 2.7 v as required by the other components in the assembly 100.

In addition, the measurement assembly 100 may also include one or more external non-volatile (E2PROM) memory chips 116 that may be used to augment the internal memory 106 of the SoC 115.

Figure 6:
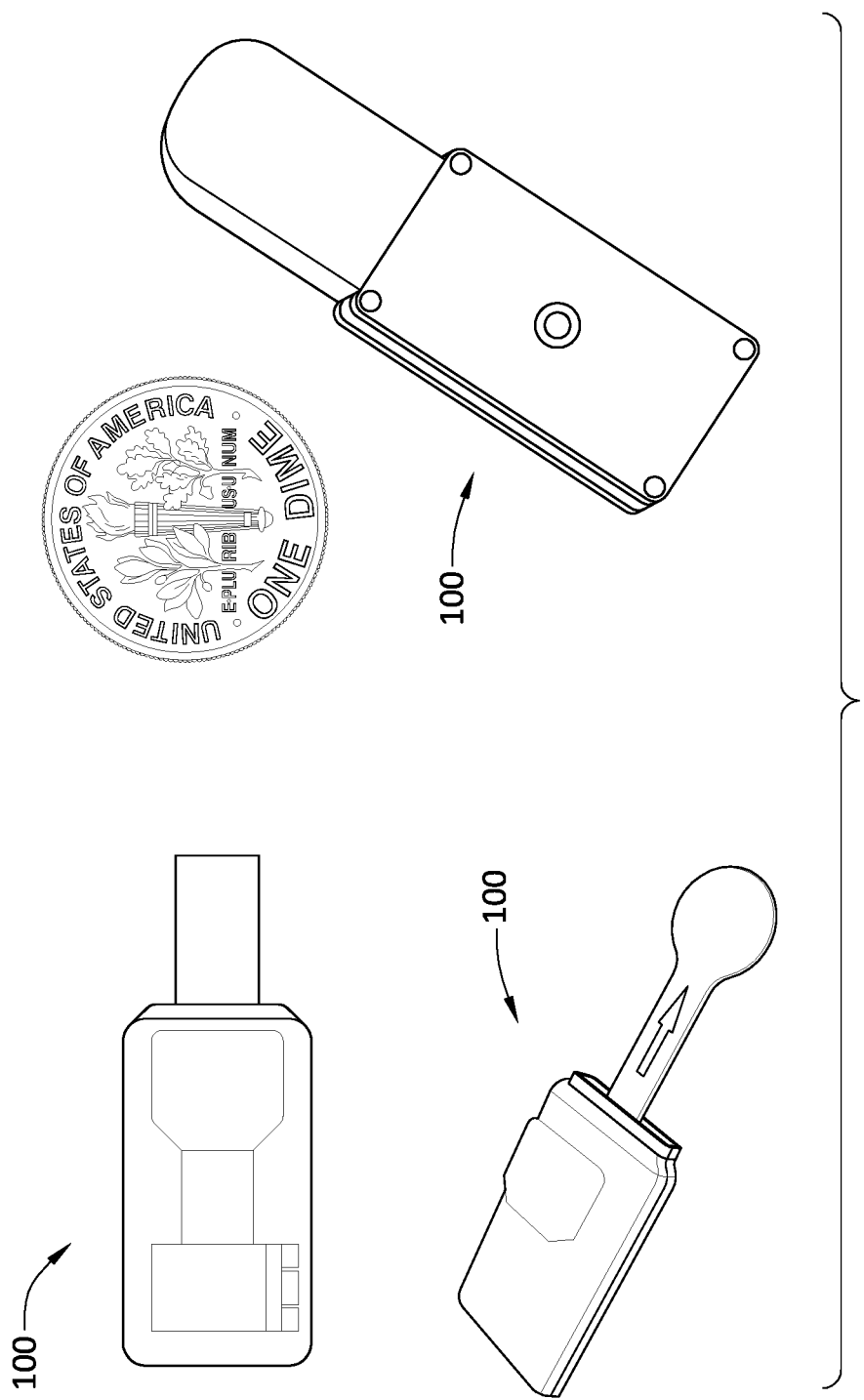

The assembly 100 may preferably be packaged as a small single unit device as shown in the different views depicted in FIG. 6.

Figure 7:
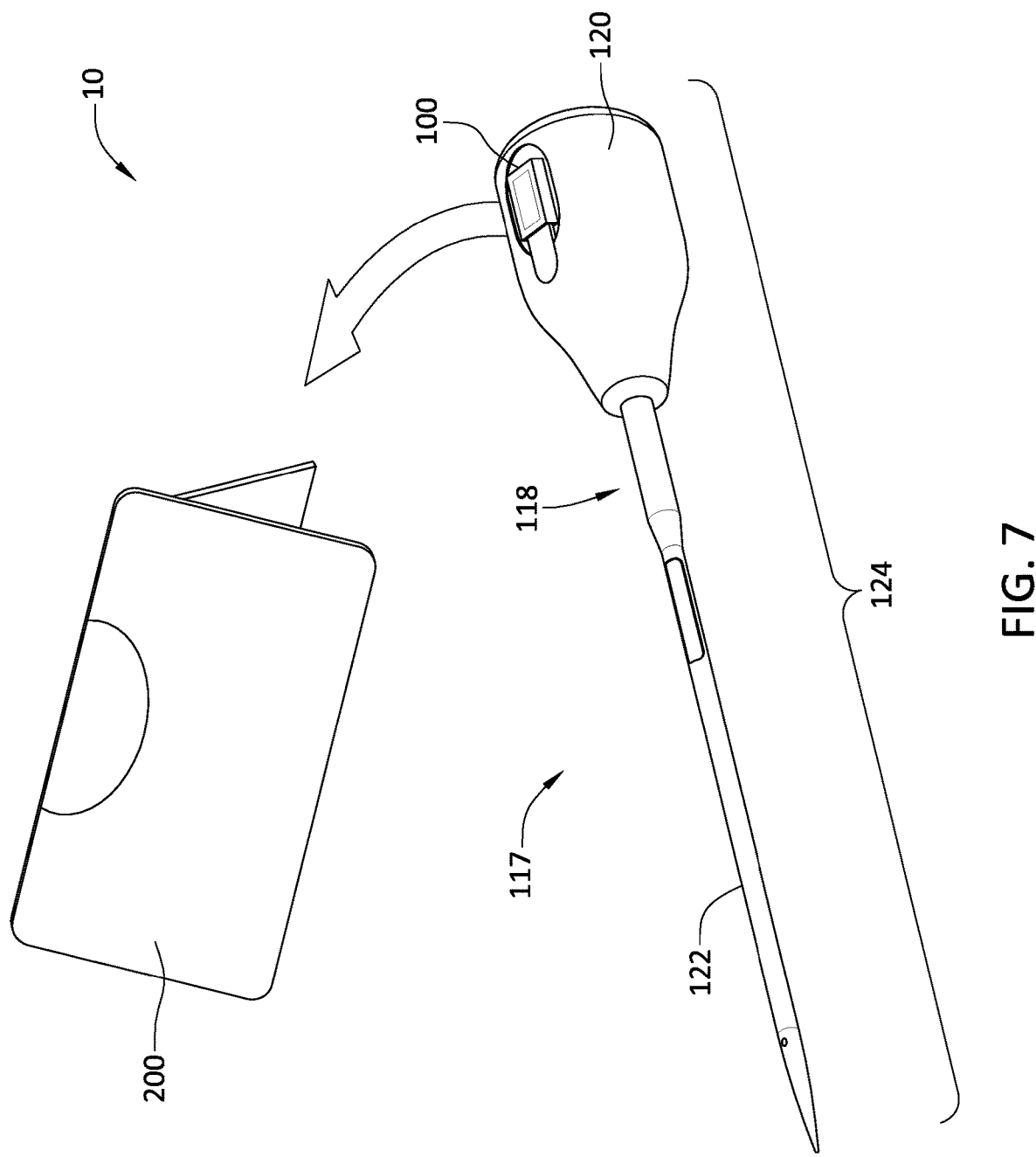
FIG. 7 shows aspects of an active instrument according to exemplary embodiments hereof.

In one exemplary embodiment hereof, the measurement assembly 100 may be configured with a handheld instrument 117, the use of which may benefit from being properly aligned. Following the example of using surgical instruments, the instrument 117 may be an awl 118 as shown in FIG. 7. The awl 118 may include a handle 120 configured with a shaft 122 as shown. The shaft 122 may include a distal tip that may be sharpened to a point with two or more sharpened side edges. As is known in the art, an awl 118 may be used to bore a hole in a material, and in this example, the awl 118 may be used to bore a pilot hole 21 through the pedicle 22 and into the vertebral body 24 of a patient's spine for the insertion of a pedicle screw 20.

The surgeon may hold the awl 118 by the handle 120 and place the distal tip of the shaft 122 at the position on the bone where the hole may be desired. The awl 118 may be rotated back and forth along the axis defined by the shaft 122 and the sharpened tip of the shaft 122 may bore the hole 21.

It can be seen that the orientation and alignment of the awl's shaft 122 during this procedure may determine the orientation and trajectory of the resulting pilot hole 21. It can also be seen that when the pedicle screw 20 may be screwed into the resulting pilot hole 21, the screw 20 may also follow the trajectory of the hole 21.

During this procedure, the measurement assembly 100 may measure the orientation and trajectory of the awl 118 (the shaft 122) and provide this information to the controller 200. The controller 200 may process the information and provide it to the user. The user of the awl 118 may then utilize this real time positional information to properly manipulate the awl 118 in the correct orientation to result in a properly oriented pilot hole 21 (and thus, a properly oriented pedicle screw 20 once inserted). This will be described in further detail in later sections.

In one presently preferred implementation as shown, the measurement assembly 100 may be configured with the handle 120 of the awl 118. However, it is understood that the assembly 100 may also be configured with the shaft 122 and/or any other element of the awl 118, and in any position on the awl 118.

The measurement assembly 100 may be attached to or otherwise configured with the instrument 117 during the manufacturing process of the instrument 117, or may be retrofitted with the instrument 117 as an after-market component. The measurement assembly 100 may be longitudinally aligned with the axis defined by the shaft 122 of the instrument so that the coordinate system used by the sensor 102 may be aligned with that of the instrument 117. This will be described in further detail in later sections. However, the assembly 100 may also be aligned in other orientations with respect to the instrument 117.

The instrument's handle 120 may include a section that may be provided to receive the assembly 100, such as a flat section, a slot, an internal cavity, or any other type of section that may accommodate the assembly 100 and allow for its secure attachment. However, this may not be required (e.g., when the assembly 100 may be configured with the instrument 117 as an after-market component). The measurement assembly 100 may be secured to the instrument (e.g., the handle 120) with adhesive (e.g., 3M sterile surgical adhesive), double-sided tape, screws, bolts, straps, bands, latches, pressure fit or any other type of attachment mechanism(s). For the purposes of this specification, an instrument 117 configured with a measurement assembly 100 may be referred to as an active instrument 124.

Prior to use, it may be preferable to calibrate the measurement assembly 100 (the active instrument 124) to verify the measurement assembly's amplitude response, system linearity and other performance characteristics over the intended range of use. In this way, the sensor 102 may be verified as performing within its specifications. The calibration may also provide a set of scale factors (calibration factors, correction factors, etc.) that may be used to correlate the electrical outputs of the assembly 100 with the real world physical coordinates of the assembly 100.

The calibration factors may be applied to the output signals of the assembly 100 in order to correct for the sensor's known deficiencies. In general, the calibration procedure may typically include the measurement and calibration of the sensor's reference sensitivity, frequency response, output bias level, transverse sensitivity, resonant frequency, time constant and other characteristics. In this way, during use, the calibration factors may be applied to the raw data received from the measurement assembly 100 and the real time angular position and trajectory of the assembly 100 may be determined within a calculated level of accuracy and uncertainty.

A reference standard, such as a standard calibrated at the United States National Institute of Standards and Technology (NIST), may be used to calibrate the active instrument 124. Alternatively, and more typically, a reference standard may be used to calibrate a transfer standard that may then be used to calibration the active instrument 124. In either case, this may allow for the absolute accuracy and the measurement uncertainty of the measurement assembly 100 (and the active instrument 124) to be assessed and optimized. It may be preferable to also test the measurement repeatability of the active instrument 124 across a series of measurements and to use this information when calculating the assembly's uncertainty.

A number of different types of calibration procedures may be used to calibrate the active instrument 124, and the proper calibration technique may be chosen depending on the type of sensor 102 employed in the assembly 100 and the instrument's desired range of use. The active instrument 124 may be calibrated prior to each use, after each use (to verify that the instrument 124 did not change or drift during use), periodically (preferably on a periodic schedule), or during any other times. It is understood that the scope of the system 10, of the measurement assembly 100 and of the active instrument 124 is not limited in any way by the types of calibration procedures used or the intervals over which the calibrations may be performed.

The Controller

In one exemplary embodiment hereof, the controller 200 may include a tablet computer, a smartphone, a mobile device, a laptop computer, a PC, a networked controller, a server (e.g., a network, backend or cloud platform), a micro-controller and any other types or combinations of types of controllers 200. The controller 200 may also include an operating system and software, scripts, applications (including mobile applications) and other types of code that the controller 200 may run or otherwise utilize.

The controller 200 may receive information from and send information to the active instrument 124 in real time. The controller 200 may be paired with the active instrument 124 via Bluetooth communications, or may utilize other types of communication protocols or methods such as RF, millimeter wave, Wi-Fi, LAN, WAN, Internet, cellular connectivity, telephony, IR or other types of communication methods, digital or analog or any combination thereof. The controller 200 may also communicate with other instrumentation (e.g., imaging instrumentation) as required using the same or different communication methods.

In one exemplary embodiment hereof, the controller 200 may receive information from the active instrument 124 indicating the instrument's real time orientation and trajectory (preferably in three dimensions) during use. The controller 200 may then process the positional data and provide it to the user in meaningful real world formats, preferably correlated with one or more three-dimensional coordinate systems (described later). The controller may also apply the calibration factors (e.g., scale factors or correction factors) of the particular active instrument 124 to increase the accuracy of the data.

Details of how the controller 200 may be used during the use of the active instrument 124 will be described in later sections.

The controller 200 may also be used to automate the calibration procedure described in prior sections. For example, the controller 200 may provide software wizards or other types of interactive tools that may guide the user during the calibration processes.

The controller 200 may also provide software wizards or other types of interactive tools that may guide the user during the use of the active instrument 124 as will be described in later sections.

Note that any number of measurement assemblies 100 may be configured with the system 10, and that each assembly 100 may be configured with a different active instrument 124. For example, a first measurement assembly 100 may be configured with an awl 117 as described above, a second measurement assembly 100 may be configured with a probe 117, a third measurement assembly 100 may be configured with a driver 117, and so on. Each measurement assembly 100 may include a unique electronic identifier (e.g., a serial number, an IP address, etc.) that the controller 200 may query, identify and record. In this way, the controller 200 may simultaneously monitor (or otherwise communicate) with each measurement assembly 100 individually.

In Use

Prior to surgery, the patient's spine may be stabilized by placing the patient on a radiolucent operating table in the prone position. With the patient's spine stabilized, imaging instrumentation (e.g., C-arm fluoroscopic imaging instrumentation) may be used to take sequences of images of the patient's spine from different perspectives. The images may then be used to construct one, two and/or three-dimensional representations of the spine. It may be preferable that the imaging instrumentation also be calibrated per its specifications as required.

In one exemplary embodiment hereof, the controller 200 (or possibly the imaging instrumentation) may use the imaging data to model, calculate or otherwise determine the proper (optimal) position, alignment (preferably in three-dimensions) and trajectory of each pilot hole for each pedicle screw 20 to be implanted. Alternatively, the controller may allow the user to interact with the controller 200 to lay out the proposed position, orientation and trajectory of each proposed pilot hole manually. For example, the controller 200 may display the representations of the patient's spine such that the user may draw (or otherwise input) the proposed position, orientation and trajectory of each pilot hole onto the layout.

Figure 8:
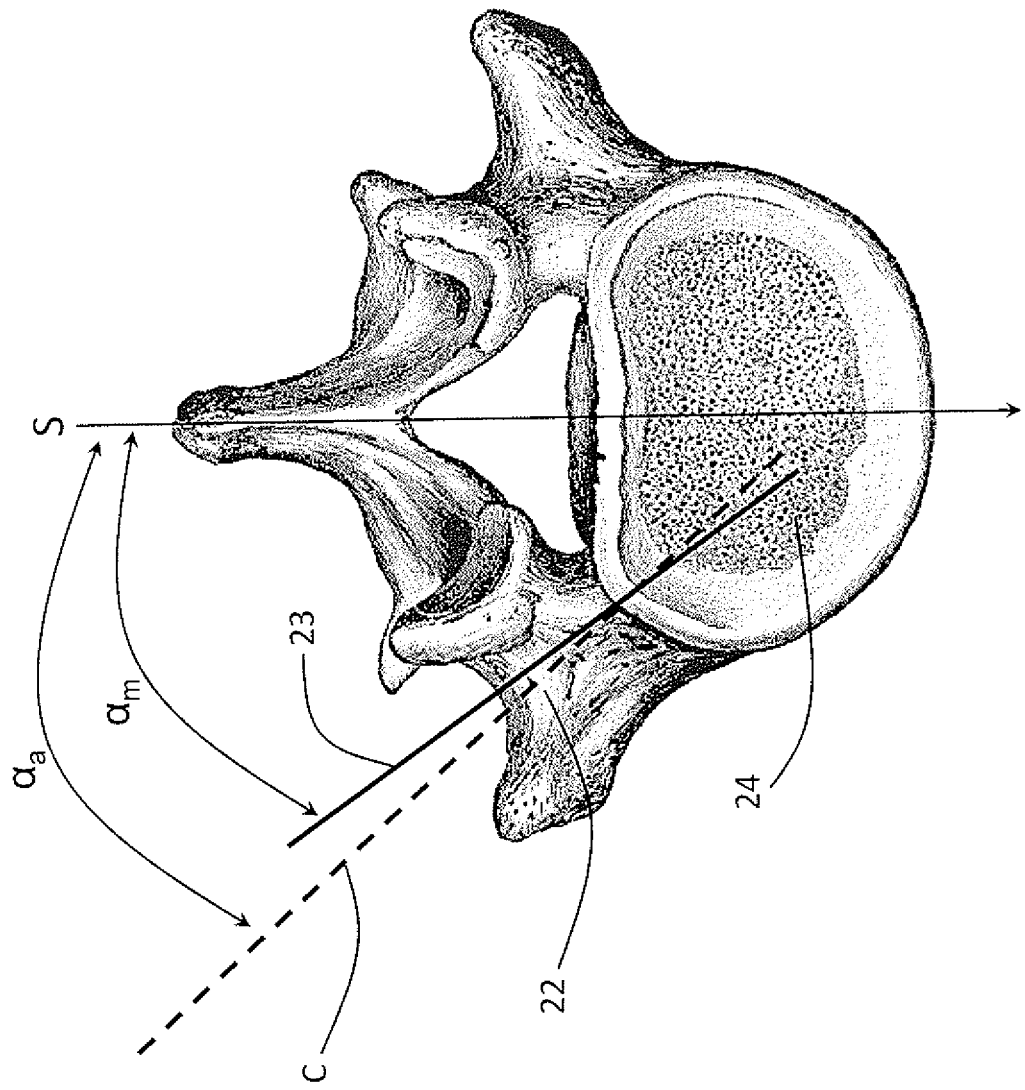
FIGS. 8 and 9 show aspects of a data layout and/or display according to exemplary embodiments hereof.

The controller 200 may also provide software wizards or other types of interactive tools that may assist the user in laying out and/or otherwise determining the position of the proposed pilot holes. For the purposes of this specification, the proposed pilot holes (whether determined by the controller 200, the user, any other system or any combination thereof) may be referred to as modeled pilot holes 23 as shown in FIG. 8.

The controller 200 may also perform quality checks on each modeled pilot hole 23 to ensure that the modeled holes 23 are indeed in the proper positions and orientations. And if potential problems are discovered, the controller 200 may bring this to the attention of the user for review. For example, the controller 200 may check to ensure that the axial and sagittal angles ($\alpha$ and $\beta$ respectively) of each pedicle screw 20 are correct and that no cortical perforations exist. The controller 200 may also ensure that the pedicle screws 20 may be properly aligned with respect to one another such that the linkage unit 26 may be attached between the screws 20 without obstruction and without applying undesired strain or torque on the screws 20 or on the patient's spinal column 28.

The position and alignment information for each modeled pilot hole 23 may include, but may not be limited to, the modeled pilot hole 23 entry point information, angular orientation, trajectory information, length information, the location, orientation and/or position of any adjacent pedicle screw pilot holes 23, the location, orientation and/or position of any associated linkage unit(s) 26, as well as other information and/or any combinations of information thereof. It may be preferable that the modeled orientation and trajectory of each modeled pilot hole 23 describe/show the hole 23 as passing through the pedicle 22 and into the vertebral body 24 without cortical perforations (as shown in FIG. 2A). The information may be complex (vector) information.

As is known in the art, three commonly used coordinate systems may be used in imaging applications and surgical procedures, including but not limited to, a world coordinate system, the anatomical coordinate system and the image coordinate system. The world coordinate system may typically include a Cartesian coordinate system and may be used to represent the position and orientation of the patient. The anatomical coordinate system (also referred to as the patient coordinate system) may consist of three planes that describe the standard anatomical position of a human body: 1) the axial plane may be parallel to the ground and may separate the head (Superior) from the feet (Inferior), 2) the coronal plane may be perpendicular to the ground and may separate the front (Anterior) from the back (Posterior), and 3) the sagittal plane may be perpendicular to the ground and may separate the Left from the Right. The image coordinate system may describe how each image was acquired with respect to the anatomy, and may consist of an origin, an i-axis increasing to the right, a j-axis increasing to the bottom, and a k-axis increasing backwards (all orthogonally).

It may be preferable that the coordinate systems used by the various instrumentation (e.g., the active instrument 124, the controller 200, the fluoroscopic imaging system, etc.) be correlated. In this way, real time angular orientation and trajectory data taken from the active instrument 124 may be accurately correlated and overlaid with the imaging data taken by the fluoroscopic imaging system. This may also allow the surgeon to understand the coordinate system he/she may use while manipulating the active instrument 124. For example, the surgeon may manipulate the axial angle $\alpha$ (FIG. 2) and the sagittal angle $\beta$ (FIG. 1) of the active instrument 124 with respect to a vertical reference such as a plumb line. The plumb line may be generally parallel or generally correspond to the vector that may represent the acceleration due to the force of gravity as measured by the sensor 102 (e.g., accelerometer). The starting position of the pilot hole 21 may be determined from the modeled pilot hole 23 or from anatomical landmarks using the surgeon's personal knowledge and/or experience.

As the active instrument 124 may be used to create the pilot hole 21, the controller 200 may overlay (or utilize other types of data presentations) the real time orientation/trajectory of the active instrument 124 with the modeled pilot hole 23 orientation/trajectory in real time. For example, as shown in FIG. 8, the controller 200 may display a cross section of the patient's vertebrae taken along the axial plane with the actual axial angle $\alpha_a$ of the active instrument 124 (shown as the dashed line C) overlaid with the modeled axial angle $\alpha_m$ of the modeled pilot hole 23 (the solid line 23), each taken with respect to the vertical axis S (e.g., the plumb line along the mid-sagittal plane). Other reference planes and/or coordinate systems may also be used as a reference.

Using this information, along with the starting point information for the pilot hole 23, the surgeon may manipulate the active instrument 124 during the drilling procedure such that the instrument's orientation/trajectory may match that of the modeled pilot hole 23. This may result in a properly aligned pilot hole 21 in the patient's spine that may generally match that of the modeled hole 23.

Figure 9:
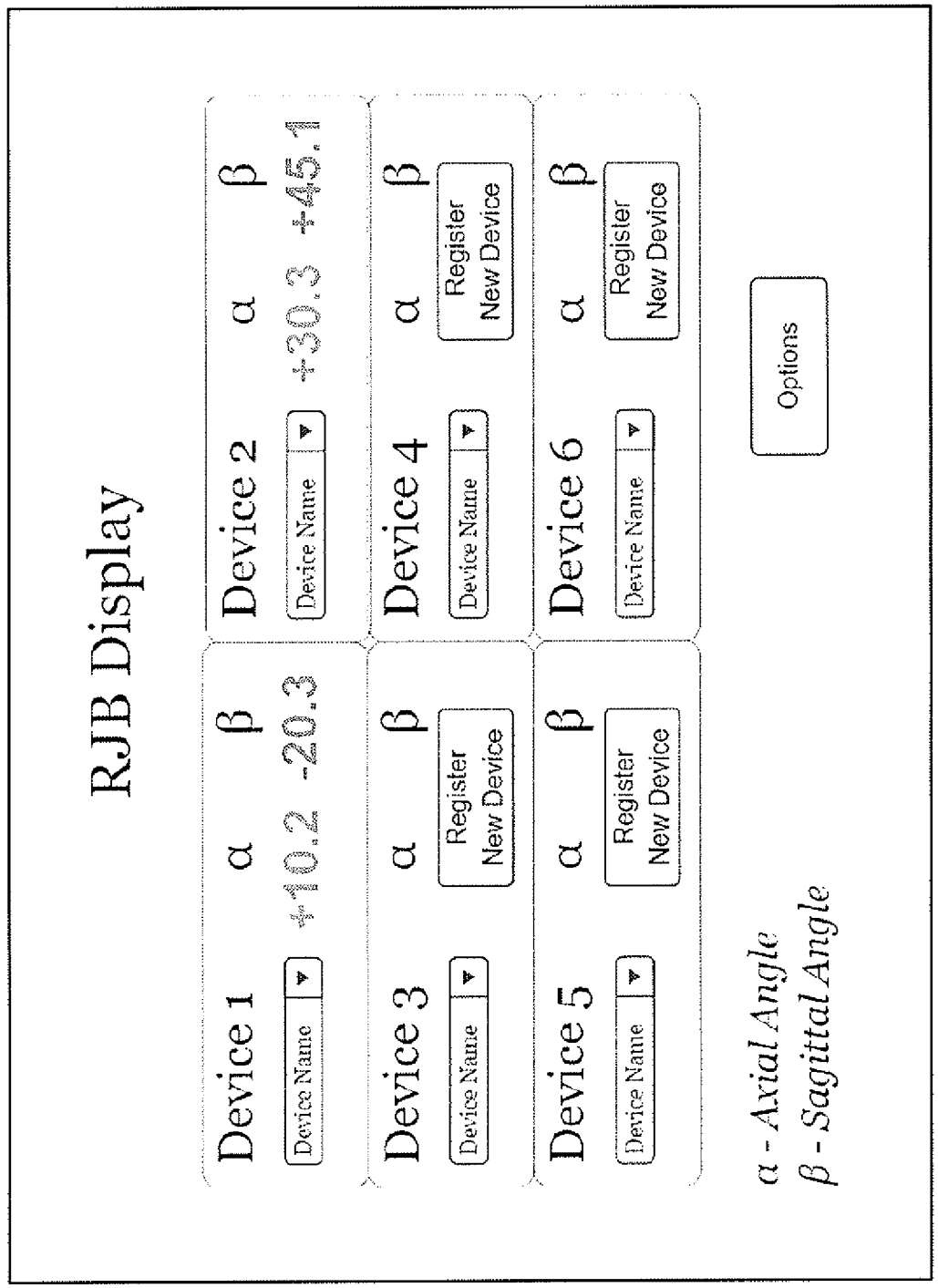

In another example as shown in FIG. 9, the controller 200 may display the angle information ($\alpha$ and $\beta$) measured by each measurement assembly 100 directly. In this way, the user may read the angles and manipulate the corresponding active instrument 124 accordingly.

FIG. 9 shows the angle information ($\alpha$ and $\beta$) for six individual measurement assemblies 100 configured with the system 10. Because each measurement assembly 100 may be configured with a different active instrument 124, the controller may display the name of the active instrument 124 along with each instrument's corresponding angular information. Other information may also be displayed. While FIG. 9 depicts positional data of six measurement assemblies 100 displayed by the controller 200, any number of measurement assemblies 100 may be configured with the system 10, and the controller 200 may display information received from any number of them.

In addition, the controller 200 may provide software wizards and/or any other types of interactive tools that may assist or otherwise guide the surgeon during the procedure.

The controller 200 may also provide other types of real time feedback to the surgeon such as warnings, e.g., if the alignment of the active instrument 124 may deviate from that of the modeled pilot hole 23 by a particular threshold. For example, if the angular orientation of the active instrument 124 may be deemed to be deviating from the modeled angular orientation of the pilot hole 23 along any plane beyond a pre-determined threshold, an audible warning may sound to alert the user. Other types of feedback and warnings such as visual, sensory, or any other type of feedback or any combination thereof may also be used.

The controller 200 may include at least one display 202 that may be easily viewable by the user of the system 10. For example, the display 202 may be positioned such that the surgeon may simply glance upward slightly in order to view the display 202 and the feedback that it may show. In another example, the display 202 of the controller 200 may be embedded into the eye glasses of the user so that the user may view both the display 202 and the patient at the same time. It is understood that the display(s) 202 may be preferably positioned anywhere where they may be viewed by at least some of the users of the system 10.

The surgeon need not be required to utilize all of the information provided by the system 10 during any particular surgery. For example, the surgeon may determine the entry point of a pilot hole 21 based on cortical landmarks and then utilize the orientation and trajectory information provided by the system 10 to bore the pilot hole 21. It is understood that some, any and/or all of the information provided by the system 10 may be utilized by the surgeon at the surgeon's discretion, and that the scope of the system 10 is not limited in any way by the information provided that the surgeon may or may not utilize.

It is understood by a person of ordinary skill in the art, upon reading this specification, that the above example describing the active instrument 124 as an awl 118 is meant for demonstration purposes, and that the active instrument 124 may be any type of instrument 117.

Figure 10:
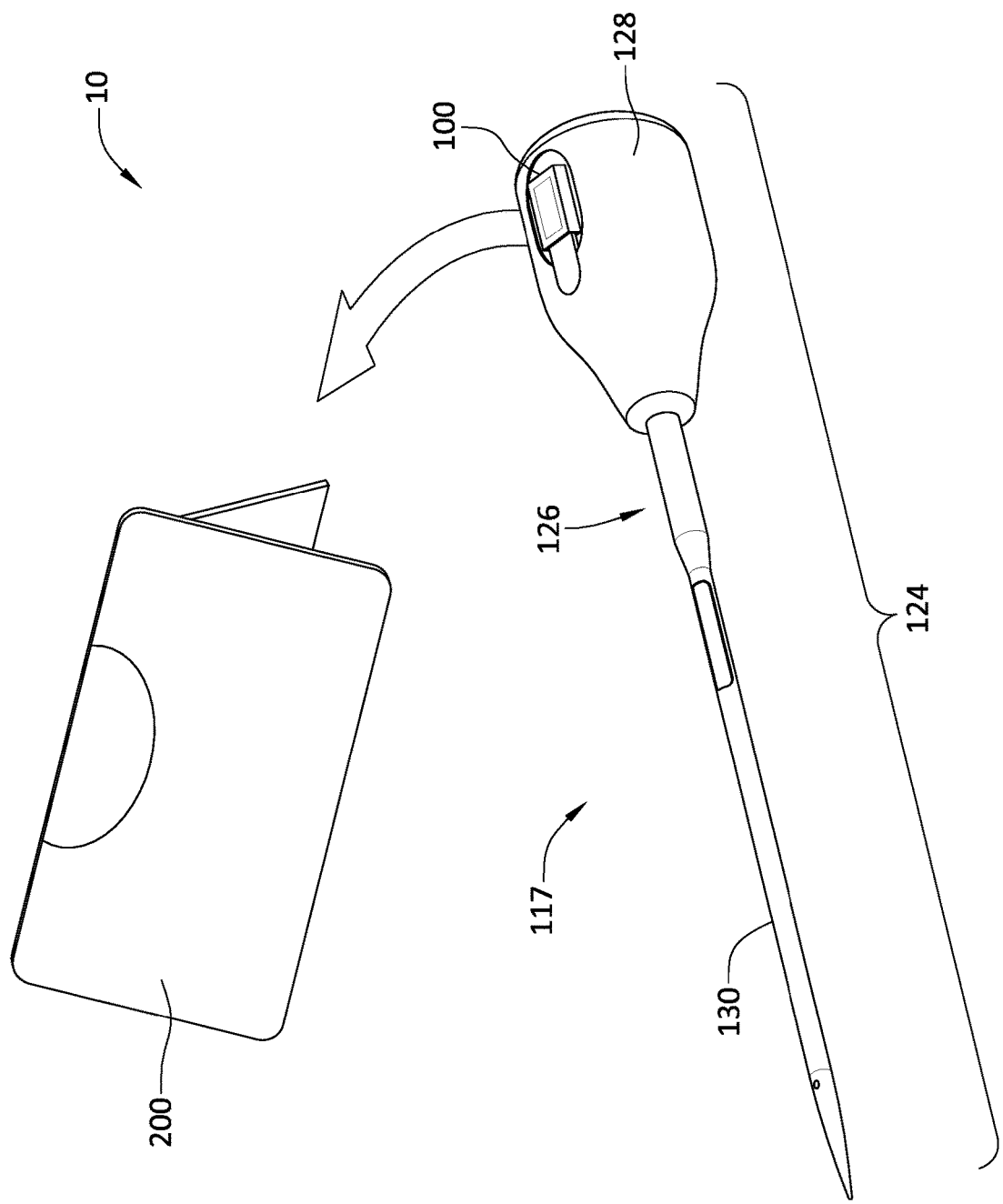
FIGS. 10-12 show aspects of an active instrument according to exemplary embodiments hereof.

For example, the instrument 117 may be a probe 126 as shown in FIG. 10. The probe 126 may include a handle 128 and a shaft 130. A measurement assembly 100 may be configured with the probe 126 (with its handle 128 or elsewhere) such that the probe 128 may be an active instrument 124.

In one preferred implementation, the probe 126 may be used to measure the angular orientation and trajectory of the bored pilot hole 21 described above. The probe 126 may be inserted into the bored pilot hole 21 and the angular orientation and trajectory of the probe 126 (and thus that of the pilot hole 21) may be measured, processed and displayed by the system 10. In this way, the angular orientation and trajectory of the pilot hole 21 may be verified as adequately correlating with the modeled pilot hole 23 as described in previous sections.

Figure 11:
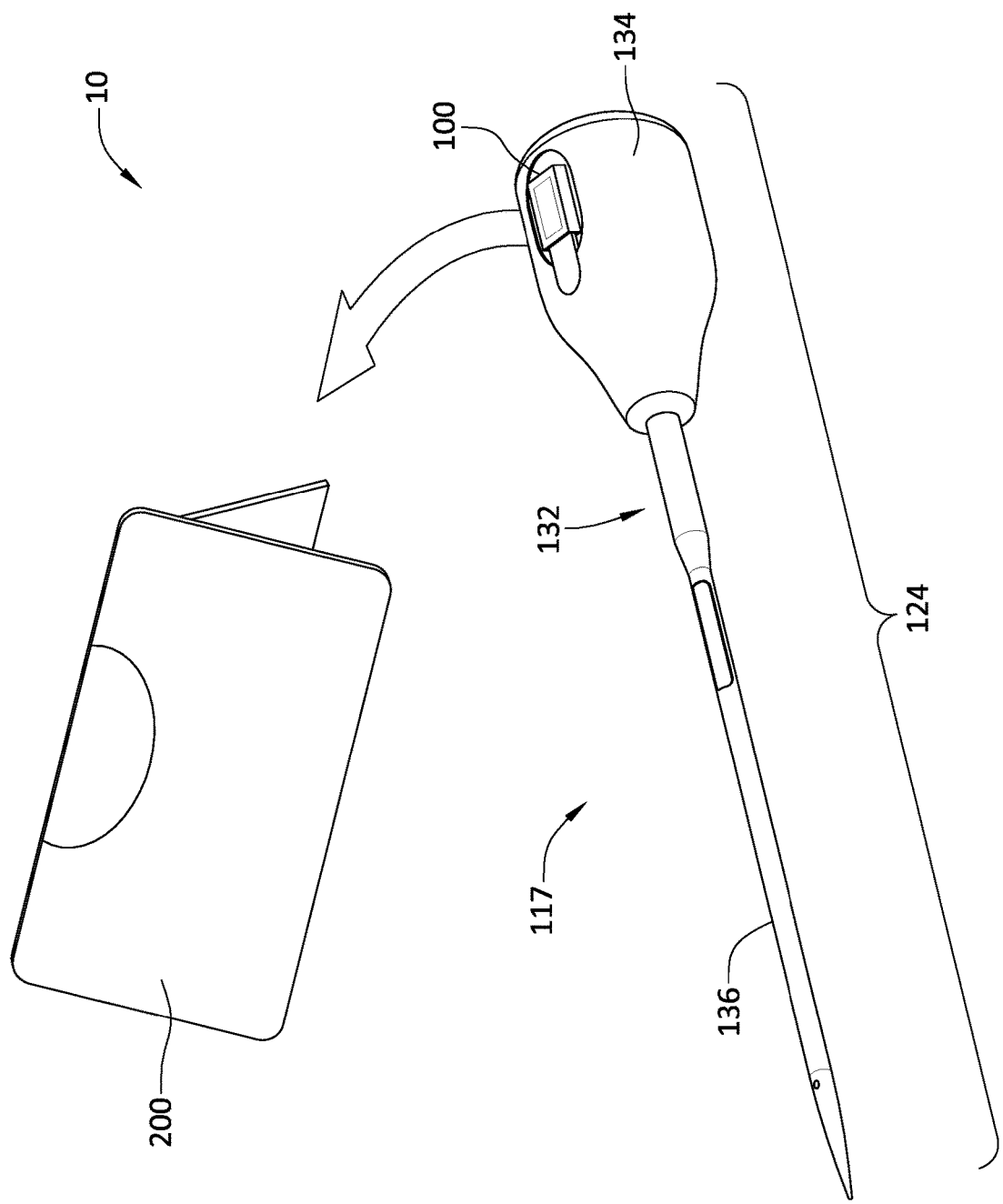

In another example as shown in FIG. 11, the instrument 117 may be a driver 132 (e.g., a screw driver) that may be used to screw each pedicle screw 20 into its corresponding pilot hole 21. The driver 132 may include a handle 134 and a shaft 136. A measurement assembly 100 may be configured with the driver 132 (e.g., with its handle 134) such that the driver 132 may be an active instrument 124. In this way, the trajectory of the screw 20 during its insertion may be monitored to match that of the modeled pilot hole 23 (and the actual pilot hole 21). This may ensure that the pedicle screw 20 may not pursue an alternate track outside the pilot hole 21 during its insertion.

Figure 12:
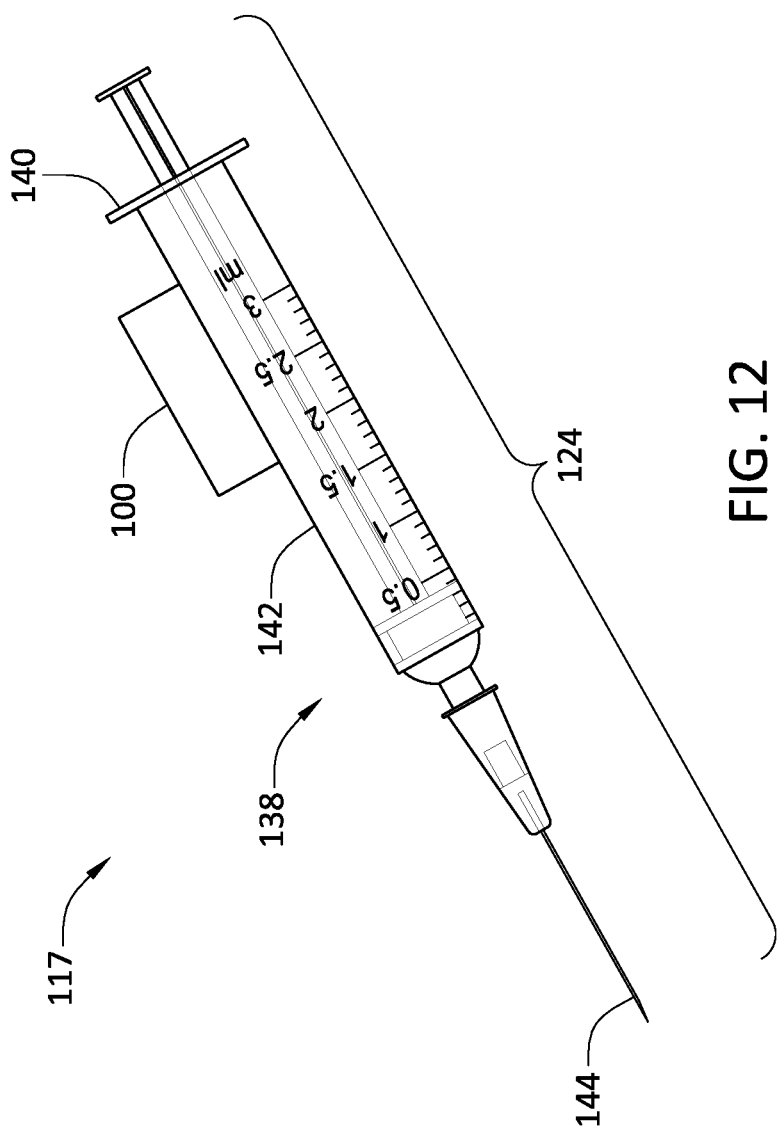

In another preferred implementation, the instrument 117 may be a hypothermic needle 138 as shown in FIG. 12. The hypodermic needle 138 may include a handle 140, a body 142 and a needle 144. A measurement assembly 100 may be configured with the hypodermic needle 132 (with its body 136 or elsewhere) such that the hypodermic needle may be an active instrument 124.

In one preferred implementation, the hypodermic needle 132 may be used to make an injection into the body of a patient. In some such procedures, it may be required that the orientation of the needle 138 be held at a particular angle in order to properly perform the injection. As an active instrument 124, the system 10 may measure, process and display the real time angular orientation of the hypodermic needle 132 such that the surgeon may manipulate it to the preferred position.

In this example, the system 10 may or may not use imaging information of the patient, and may instead use theoretical modelled data to guide the user through the procedure. Alternatively, the user may simply use the positional data provided by the system 10 and manipulate the active instrument 124 with respect to a known reference coordinate system (e.g., a vertical plumb line).

While the system 10, including the measurement assembly 100 and the controller 200, has been described above with reference to surgical procedures such as spinal stabilization surgery and injections using a hypodermic needle, other types of surgical procedures may also benefit from the use of the system 10. For example, kyphoplasty, percutaneous bone biopsies of a known lesion within a bone, neurosurgical procedures within the brain that may require stereotactic surgery, as well as other surgical procedures, may also be used with, and benefit from, the system 10.

In all of the embodiments disclosed or otherwise, the measurement assembly 100 and/or the active instrument 124 may be disposable and may be designed to be used once and then discarded. Alternatively, the measurement assembly 100 and/or the active instrument 124 may be designed to be used multiple times.

In addition, in all of the embodiments disclosed or otherwise, it may be preferable that the measurement assembly 100 and/or the active instrument 124 be sterilized and/or otherwise be provided as a sterile device.

Where a process is described herein, those of ordinary skill in the art will appreciate that the process may operate without any user intervention. In another embodiment, the process includes some human intervention (e.g., a step is performed by or with the assistance of a human).

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

As used in this description, the term "portion" means some or all. So, for example, "A portion of X" may include some of "X" or all of "X". In the context of a conversation, the term "portion" means some or all of the conversation.

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

It should be appreciated that the words "first," "second," and so on, in the description and claims, are used to distinguish or identify, and not to show a serial or numerical limitation. Similarly, letter labels (e.g., "(A)", "(B)", "(C)", and so on, or "(a)", "(b)", and so on) and/or numbers (e.g., "(i)", "(ii)", and so on) are used to assist in readability and to help distinguish and/or identify, and are not intended to otherwise limiting or to impose or imply any serial or numerical limitations or orderings. Similarly, words such as "particular," "specific," "certain," and "given," in the description and claims, if used, are to distinguish or identify, and are not intended to be otherwise limiting.

As used herein, including in the claims, the terms "multiple" and "plurality" mean "two or more," and include the case of "two." Thus, e.g., the phrase "multiple ABCs," means "two or more ABCs," and includes "two ABCs." Similarly, e.g., the phrase "multiple PQRs," means "two or more PQRs," and includes "two PQRs."

The present invention also covers the exact terms, features, values and ranges, etc. in case these terms, features, values and ranges etc. are used in conjunction with terms such as about, around, generally, substantially, essentially, at least etc. (i.e., "about 3" or "approximately 3" shall also cover exactly 3 or "substantially constant" shall also cover exactly constant).

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components unless specifically so stated.

It will be appreciated that variations to the embodiments of the invention can be made while still falling within the scope of the invention. Alternative features serving the same, equivalent or similar purpose can replace features disclosed in the specification, unless stated otherwise. Thus, unless stated otherwise, each feature disclosed represents one example of a generic series of equivalent or similar features.

The present invention also covers the exact terms, features, values and ranges, etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

Use of exemplary language, such as "for instance", "such as", "for example" ("e.g.,") and the like, is merely intended to better illustrate the invention and does not indicate a limitation on the scope of the invention unless specifically so claimed.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

What is claimed is:

1. A system for providing feedback regarding the angular orientation of a handheld instrument, comprising:
    a measurement sensor assembly that includes an integrated circuit, that is configured to attach to the handheld instrument, that measures the angular orientation of the handheld instrument when attached thereto, and that provides information based on the measured angular orientation; and
    an application that is configured to run on a controller in communication with the measurement sensor assembly to enable the controller to process the information and provide a visual display of the measured angular orientation.

2. The system of claim 1 wherein the measurement sensor assembly includes a unique electronic identifier for monitoring by the controller.

3. The system of claim 1 wherein the measurement sensor assembly includes a chip and an accelerometer, wherein the integrated circuit is configured on the chip, and the accelerometer is mounted on the chip.

4. The system of claim 1 wherein the measurement sensor assembly includes at least one gyroscope.

5. The system of claim 1 wherein the measured angular orientation is an orientation in three-dimensional space.

6. The system of claim 1 wherein the visual display of the measured angular orientation includes axial and sagittal angles of the handheld instrument.

7. An angular measurement sensor adapted to measure the angular orientation of a surgical instrument, the angular measurement sensor comprising:
    a package that is configured to be attached to the surgical instrument when attached thereto, wherein the package contains:
        an accelerometer that measures the angular orientation of the surgical instrument, and that outputs a signal based on the measured angular orientation;
        a transmitter that transmits information regarding the angular orientation of the surgical instrument based on the signal or processing of the signal; and
        a power supply comprising a battery, wherein the angular measurement sensor is operable only for a life of the battery;
    wherein the angular measurement sensor includes a unique electronic identifier.

8. The angular measurement sensor of claim 7, wherein the unique electronic identifier associates the angular measurement sensor with only the surgical instrument to which the package is attached.

9. The angular measurement sensor of claim 7 wherein the angular measurement sensor is operable for only one use and/or is disposable.

10. The angular measurement sensor of claim 7 wherein the transmitter transmits information regarding the axial angle and sagittal angle of the surgical instrument.

11. The angular measurement sensor of claim 7 wherein the package is small enough so that it partially fits within a profile of the surgical instrument when attached thereto.

12. The angular measurement sensor of claim 7 wherein the signal output by the accelerometer is also based on trajectory information.

13. The angular measurement sensor of claim 7 wherein the transmitter is a Bluetooth enabled transmitter.

14. A system to perform surgery including a handheld surgical instrument adapted to provide information regarding its angular orientation, the handheld surgical instrument comprising:
    a handle;
    an instrument attached to the handle; and
    a measurement sensor that is attached to the handle, that measures the angular orientation of the handheld surgical instrument based on the amount of static acceleration of the handheld surgical instrument due to gravity, that includes a unique electronic identifier and that outputs a signal based on the measured angular orientation.

15. The system to perform surgery of claim 14 further including a controller in communication with the measurement sensor, wherein the controller monitors the measurement sensor by the unique electronic identifier, and wherein the controller receives the signal and provides a visual display of the angular orientation of the surgical instrument.

16. The surgical instrument of claim 15 wherein the visual display includes axial and sagittal angles of the handheld surgical instrument.

17. The system of claim 14 wherein the handle includes a flat section, a slot or an internal cavity, and the measurement sensor is securely attached thereto.

18. The system of claim 14 wherein the instrument comprises an awl, a probe or a screwdriver.

19. The system of claim 14 wherein the measurement sensor includes at least one gyroscope.

20. The system of claim 14 wherein the measurement sensor includes a battery and the measurement sensor is operable only for a life of the battery.

21. The surgical instrument of claim 14 wherein the measurement sensor comprises piezoelectric, piezoresistive or capacitive components that convert mechanical or physical motion into an electrical signal.

22. A method for displaying the angular orientation of aligning a handheld surgical instrument comprising:
   a measurement sensor assembly that is attached to the handheld instrument, that includes an accelerometer which measures the angular orientation of the handheld instrument in three dimensions in relation to gravity, and that provides information regarding the axial and sagittal angles of the handheld instrument in relation to the patient's spine based on the measured angular orientation; and
   a controller that receives the information from the measurement sensor assembly, and that correlates the information to provide a visual display of the axial and sagittal angles of the handheld instrument in relation to the patient's spine;
   the method comprising:
   using the measurement sensor assembly to measure the angular orientation of the handheld instrument;
   providing the information to the controller;
   using the controller to correlate the information; and
   providing a visual display of the axial and sagittal angles of the handheld instrument in relation to the patient's spine.

23. The method of claim 22 further comprising correlating the information with previously taken spinal imaging data.

24. A system for displaying the angular orientation of a handheld instrument during spinal surgery, comprising:
   a measurement sensor assembly that is attached to the handheld instrument, that includes an integrated circuit, that measures the angular orientation of the handheld instrument, and that provides information based on the measured angular orientation; and
   a controller that receives the information from the measurement sensor assembly, that correlates the information with previously taken spinal imaging data, and that provides a visual display of the axial and sagittal angles of the handheld instrument relative to the spine based on the correlated information.

25. The system of claim 24 wherein the controller correlates the information with previously taken fluoroscopic spinal imaging data, and the displayed axial and sagittal angles of the handheld instrument are based on the correlated information.

26. A system for displaying the angular orientation of a handheld instrument, in relation to a patient's spine, comprising:
   a measurement sensor assembly that is attached to the handheld instrument, that includes an accelerometer which measures the angular orientation of the handheld instrument in three dimensions in relation to gravity, and that provides information regarding the axial and sagittal angles of the handheld instrument in relation to the patient's spine based on the measured angular orientation; and
   a controller that receives the information from the measurement sensor assembly, and that correlates the information to provide a visual display of the axial and sagittal angles of the handheld instrument in relation to the patient's spine.

27. The system of claim 26, wherein a processor correlates the information with previously taken spinal imaging data.

28. The system of claim 27, wherein the previously taken spinal imaging data is previously taken fluoroscopic spinal imaging data.

* * * * *